United States Patent
Botterweck et al.

(10) Patent No.: US 7,787,669 B2
(45) Date of Patent: Aug. 31, 2010

(54) RECONSTRUCTION OF LOCAL PATIENT DOSES IN COMPUTED TOMOGRAPHY

(75) Inventors: Henrik Botterweck, Aachen (DE); Lothar Spies, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 485 days.

(21) Appl. No.: 10/543,567

(22) PCT Filed: Jan. 19, 2004

(86) PCT No.: PCT/IB2004/000176

§ 371 (c)(1),
(2), (4) Date: Jul. 27, 2005

(87) PCT Pub. No.: WO2004/067091

PCT Pub. Date: Aug. 12, 2004

(65) Prior Publication Data

US 2006/0098856 A1    May 11, 2006

(30) Foreign Application Priority Data

Jan. 30, 2003    (EP)  .................................. 03100190

(51) Int. Cl.
*G06K 9/00* (2006.01)
(52) U.S. Cl. .............................. 382/128; 128/922; 378/4
(58) Field of Classification Search .................. 382/131, 382/130, 100, 128, 132; 600/443; 128/922; 378/4–27
See application file for complete search history.

(56) References Cited

U.S. PATENT DOCUMENTS

| 5,317,616 | A | * | 5/1994 | Swerdloff et al. ............. 378/65 |
| 5,418,827 | A | * | 5/1995 | Deasy et al. .................. 378/65 |
| 5,459,769 | A | * | 10/1995 | Brown .......................... 378/4 |
| 5,548,627 | A |   | 8/1996 | Swerdloff et al. |
| 5,661,773 | A | * | 8/1997 | Swerdloff et al. ............. 378/65 |
| 6,222,905 | B1 |   | 4/2001 | Yoda et al. |

(Continued)

FOREIGN PATENT DOCUMENTS

| EP | 0 804 943 A2 | 11/1997 |
| WO | WO 98/31423 A1 | 7/1998 |
| WO | WO 00/07667 A1 | 2/2000 |

OTHER PUBLICATIONS

Kapatoes, J. ("The limitations of dose reconstruction without treatment imaging" Engineering in Medicine and Biology Society, 2000. Proceedings of the 22nd Annual International Conference of the IEEE vol. 1, Jul. 23-28, 2000 pp. 108-111 vol. 1).*

(Continued)

*Primary Examiner*—Anand Bhatnagar

(57) ABSTRACT

In order to reduce an x-ray dose applied to a patient, it is necessary to know the dose absorbed by the patient. According to the present invention, there is provided a method of determining a local patient dose applied to a patient where after the reconstruction of the scan data into a diagnostic image, the scan data are backprojected into the patient volume, using the attenuation information of the diagnostic image to form a spatially varying photon fluence map. In parallel, the diagnostic image is segmented into anatomical structures to which dose-weighting factors are assigned. The locally absorbed dose is then calculated on the basis of the fluence map and the corresponding dose weights.

20 Claims, 4 Drawing Sheets

U.S. PATENT DOCUMENTS

| | | | |
|---|---|---|---|
| 6,404,844 B1 | 6/2002 | Horiuchi et al. | |
| 6,661,870 B2 * | 12/2003 | Kapatoes et al. | 378/65 |
| 2003/0095696 A1 * | 5/2003 | Reeves et al. | 382/131 |
| 2004/0101104 A1 * | 5/2004 | Avinash et al. | 378/98.12 |

OTHER PUBLICATIONS

Kapatoes, "The limitations of dose reconstruction without treatment imaging", Engineering in Medicine and Biology Society, 2000. Proceedings of the 22nd Annual International Conference of the IEEE (vol. 1, Jul. 23-28, 2000 pp. 108-111 vol. 1.).*

Mackie,Image guidance for precise conformal radiotherapy, May 2003, International Journal of Radiation Oncology*Biology*Physics, vol. 56, Issue 1,pp. 89-105.*

Rafael C. Gonzalez, Digital Image Processing, Nov. 9, 2001, Prentice Hall, 2/E, pp. 29,30,50,109,110,111,627,629,630.*

Andrew G. Webb, "Introduction to Biomedical Imaging"; Dec. 26, 2002; p. 47.*

* cited by examiner

RECONSTRUCTION OF LOCAL PATIENT DOSES IN COMPUTED TOMOGRAPHY

The present invention relates generally to methods and apparatus for "computed tomography" (CT) and other radiation imaging systems and more particularly to a method of determining a local patient dose applied to a patient in computed tomography, an imaging processing device and a computer program for an image processing device.

In at least some CT imaging system configurations, an x-ray source projects a fan-shaped beam such that it is collimated to lie within an X-Y plane of a Cartesian coordinate system, which is usually referred to as the "imaging plane". The x-ray beam passes through an object being imaged, such as a medical patient. The beam, after being attenuated by the object, impinges upon an array of radiation detectors. The intensity of the attenuated beam radiation received at a detector array is dependent upon the attenuation of the x-ray beam by the object being imaged. Each detector element of the detector array generates an electrical signal indicating the beam attenuation at the detector location. The attenuation measurements from all the detectors are acquired separately to produce a transmission profile and represent scan data.

In known third generation CT systems, the x-ray source and the detector array are rotated with a gantry within the imaging plane and around the object to be imaged, such that an angle at which the x-ray beam intersects the object changes constantly. The used x-ray sources usually include x-ray tubes, which emit the x-ray beam at a focal spot. X-ray detectors may include a collimator for collimating x-ray beams received at the detector, a scintillator adjacent to the collimator and photodetectors adjacent to the scintillator. A group of x-ray attenuation measurements, i.e. projection data from the detector array at one ganrty angle is referred to as a "view". A "scan" of the object for generating the necessary scan data comprises a set of views made at different gantry angles, or view angles, during one revolution of the x-ray source and detector.

In an axial scan, the projection data is processed to construct an image that corresponds to a two-dimensional slice taken through the object. A known method for reconstructing an image from a set of projection data or scan data is the filtered back projection technique. This process converts the attenuation measurements from a scan into integers called "CT numbers" or "Hounsfield units", which are used to control grey values of a corresponding diagnostic image.

In other words, in the known CT scanners, the recorded projections acquired during an object or patient scan (scan data) are mathematically reconstructed into a tomographic image with grey levels indicating Hounsfield units. The tomographic image is used by, for example, a clinician for diagnostic purposes and is referred to as the diagnostic image in the following.

Currently, attempts are made to reduce doses applied to patients during CT scans. However, an identification of an exceeding dose and an optimation of the dose applied to the patient during the scan requires the exact knowledge of the doses actually applied to the patient during the scan.

The program "WinDose" (Kalendar, W. A., Schmidt B., Zankl M., Schmidt M. (1999), A PC program for estimating organdose and effective dose values in computed tomography. European Radiology 9: 555-562) is a PC program for estimating organdose and effective dose values in computed tomography and calculates the patient dose applied to the patient, on the basis of only a few parameters of the patient. Primarily, these parameters are referring to the circumference and weight of the patient and the settings of the x-ray tube, such as the applied power (mA, kVp). Then, on the basis of tables, and by using a Monte Carlo simulation, which has been computed with respect to a standard patient having a standard shape, an integral dose of the most important organs may be determined. However, this computer program does not deliver sufficient results in case the patient differs from the standard data, for example in pediatrics.

WO 00/07667 relates to a radiotherapy verification system, wherein a dose delivered to the patient may be computed on the basis of a model of the patient to estimate values of energy fluence prior to absorption by the patient and overlapping of the various radiation beams passing through the patient. A model may be constructed from a known geometry of the radiation therapy machine and estimated properties of the patient or standard patient as deduced from a pre-treatment tomography. Accordingly, in order to compute a dose delivered to the person in the system known from WO 00/07667, either a standard patient has to be used for the computation of the dose resulting in the same insufficient results as the program "WinDose" or a pre-treatment tomogram has to be carried out which increases the overall dose applied to the patient.

It is an object of the present invention to determine and minimize a local patient dose applied to a patient in computed tomography.

According to an exemplary embodiment of the present invention, this object is solved with a method of determining a local patient dose applied to a patient in computed tomography comprising the steps of segmenting a diagnostic image of an area of interest of the patient and determining a dose image showing local patient doses applied to the patient by using the segmented diagnostic image. Due to the segmentation of the diagnostic image, a local dose delivery to critical and dose-sensitive organs may be determined very accurately and may enable an improved patient dose management.

According to another exemplary embodiment of the present invention as set forth in claim 2, anatomical structures are segmented in the diagnostic image and dose-weighting factors are assigned to the anatomical structures. Advantageously, this allows, for example, for distinguishing between sensitive and non-sensitive organs of the patient and allows for a very exact determination of the local patient dose.

According to yet another exemplary embodiment according to claim 3 of the present invention, a fluence map is determined. Advantageously, this allows a clinician to immediately determine and to monitor a local dose delivery to critical and dose-sensitive organs of the patient.

According to another exemplary embodiment of the present invention according to claim 4, the dose image is determined on the basis of the fluence map and the dose-weighting factors. This allows for a very accurate determination of the local patient dose applied to the patient while being very effective and efficient with respect to computational efforts. Thus, this exemplary embodiment of the present invention provides for a very simple and fast method to determine the local patient dose.

According to another exemplary embodiment of the present invention as set forth in claim 5, the diagnostic image has grey levels indicating Hounsfield units and the fluence map is determined by filtering the scan data appropriately and back-projecting it using the diagnostic image. This allows for a simple determination of the fluence map. Further, this exemplary embodiment of the present invention allows for a very accurate determination of the fluence map.

According to another exemplary embodiment of the present invention, an image processing device is provided with the features of claim 6, which allows for a very accurate determination of local patient dose.

Further exemplary embodiments of the image processing device according to the present invention, as set forth in claims 6, 7 and 8, provide for a fast and efficient determination of the local patient dose applied to the patient while minimizing computation efforts and while being very accurate.

According to another exemplary embodiment of the present invention as set forth in claim 10, a computer program for an image processing device is provided, executing the method according to the present invention.

As described above, CT scanner devices usually produce a diagnostic image on the basis of the recorded projections acquired during a patient scan, with grey levels indicating Hounsfield units. However, Hounsfield units are proportional to linear attenuation coefficients of the underlining anatomical structure, but differ from the energy absorbed locally in the patient. Consequently, the absorbed dose distribution will deviate in a non-linear way from the underlying diagnostic image. According to the present invention, a method and apparatus are provided which are able to reconstruct the local dose distribution on the basis of the registered projections (scan data). It may be seen as the gist of the invention that the method/apparatus makes twofold use of the scan data as follows: After reconstruction of the scan data into a diagnostic image, for another time, the scan data are back-projected into the patient volume using the attenuation information of the diagnostic image forming a spatially varying photon fluence map as being produced by the x-ray beam incident on the patient. In parallel, the diagnostic image is segmented into anatomical structures (regions with approximately constant attenuation). Dose-weighting factors are assigned which account for the difference between locally absorbed energy and photon attenuation. The locally absorbed dose is then calculated on the basis of the fluence map and the corresponding dose weights.

These and other aspects of the present invention will become apparent from and elucidated with reference to the embodiments described hereinafter.

Exemplary embodiments of the present invention will be described in the following, with reference to the following drawings.

Figure 1:
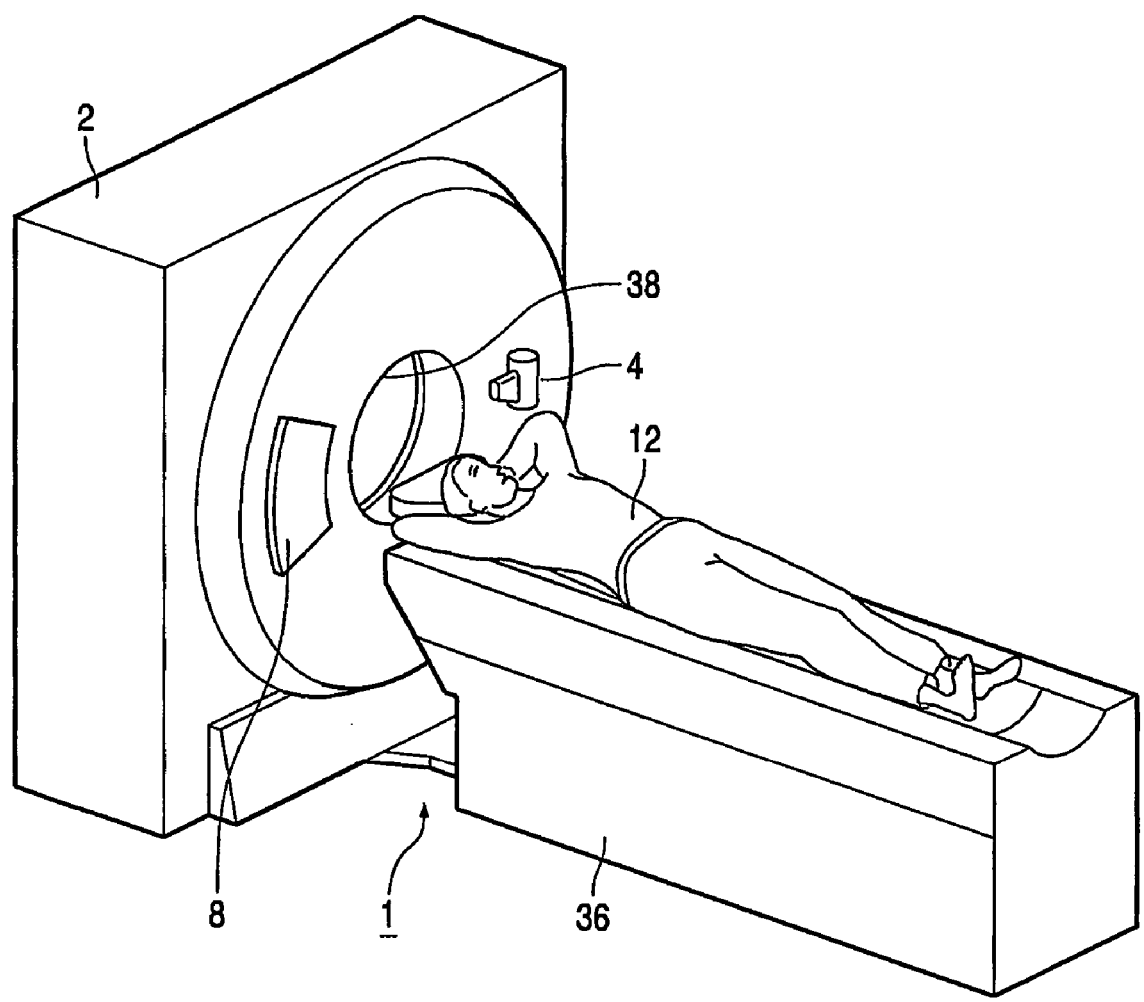
FIG. 1 shows a pictorial view of a CT imaging system.
Figure 2:
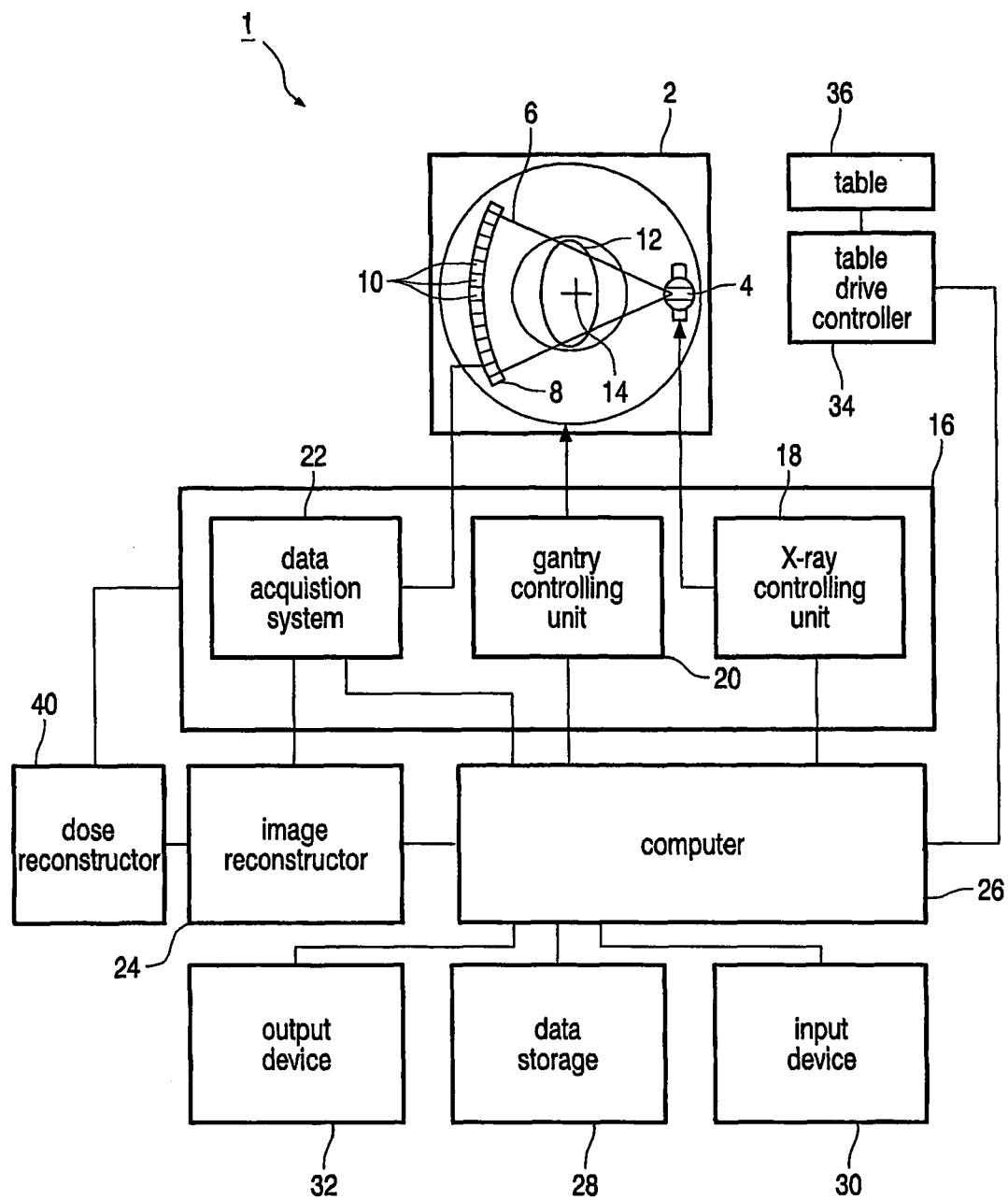
FIG. 2 shows a block schematic diagram of the system illustrated in FIG. 1.

Referring to FIGS. 1 and 2, a computed tomography (CT) imaging system 1 is shown. It includes a gantry 2, representative of a "third generation" CT scanner. Gantry 2 has an x-ray source 4 that projects a beam of x-rays 6 towards a detector array 8 on the opposite side of the gantry 2. The detector array 8 is formed by a plurality of detector elements 10, which together sense the projected x-rays that pass through an object, such as depicted in FIG. 1, a medical patient 12. Each detector element 10 produces an electrical signal that represents an intensity of an impinging x-ray beam and hence the attenuation of the beam as it passes through the object or patient 12. During a scan to acquire x-ray projection data, the gantry 2 and the components mounted thereon, namely the x-ray source 4 and the detector 8 with the detector elements 10, rotate about a center of rotation 14. In the embodiment shown in FIG. 2, a plurality of detector elements 10 are arranged in one row, so that projection data corresponding to a single image slice is acquired during a scan. According to another embodiment, the detector elements 10 may be arranged in a plurality of parallel rows, so that projection data corresponding to a plurality of parallel slices can be acquired simultaneously during a scan.

The rotation of the gantry 2 and the operation of x-ray source 4 are controlled by a control mechanism 16 of the CT system 1. The control mechanism 16 includes an x-ray controlling unit 18, which provides the necessary power and timing signals to the x-ray source 4 and a gantry controlling unit 20, which controls the rotational speed and position of gantry 2 by generating and providing respective control signals to the drive of the gantry 2.

Reference number 22 designates a data acquisition system provided in the control mechanism (16). The data acquisition system 22 samples analogue data from the detector elements 10 and converts the data to digital signals for subsequent processing.

Furthermore, there is provided an image reconstructuor 24 which receives samples in digitised x-ray data from the data acquisition system 22 and performs a high-speed image recognition. Also, there is provided a dose reconstructor 40 for reconstructing a dose which is connected to the data acquisitions system 22 and to the image reconstructor 24. Instead of providing a separate image reconstructor 24 and a separate dose reconstructor 40, the function and operation of the image reconstructor 24 and the dose reconstructor 40 may be combined in a separate device or may also be accommodated in the computer 26.

The reconstructed image is applied as an input to the computer 26 which stores the image in a mass storage device 28, such as a hard disc drive or a floppy drive.

The computer 26 also receives commands and scanning parameters from an operator via an input device 30, such as a keyboard or pointer device. Furthermore, there may be provided an output device 32 such as a display or printer, in order to allow the operator to observe the reconstructed image and other data provided by the computer 26. The operator supplied commands and parameters are used by computer 26 to provide control signals and information to the data acquisition system 22, to the x-ray controller 18 and to the gantry controlling unit 20. Furthermore, the computer 26 generates output signals output to a table drive controller 34 for controlling a movement, position and inclination of the table 36, by providing respective control signals to drive units of the table 36. Thus, the computer 26 controls the position and movement of the patient 12 in a gantry opening 38 of the gantry 2. In particular, by the movement of the table 36, the patient 12 is moved through the gantry opening 38.

The data acquisition system 22, the gantry controlling unit 20, the x-ray controlling unit 18, the image reconstructor 24, dose reconstructor 40 and the table drive controller 34 may all be realized by means of suitable processors or programmable logic controllers, such as EPLDs distributed by ALTERA in combination with respective power amplifiers. However, all the operations and functions provided by the data acquisition system 22, the gantry controlling unit 20, the x-ray controlling unit 18, the image reconstructor 24, the dose reconstructor 40, the output device 32, the data storage 28, the input device 30, the computer 26 and the table drive controller 34, may be realized by means of a computer such as a personal computer with, for example, a Pentium processor.

Figure 3:
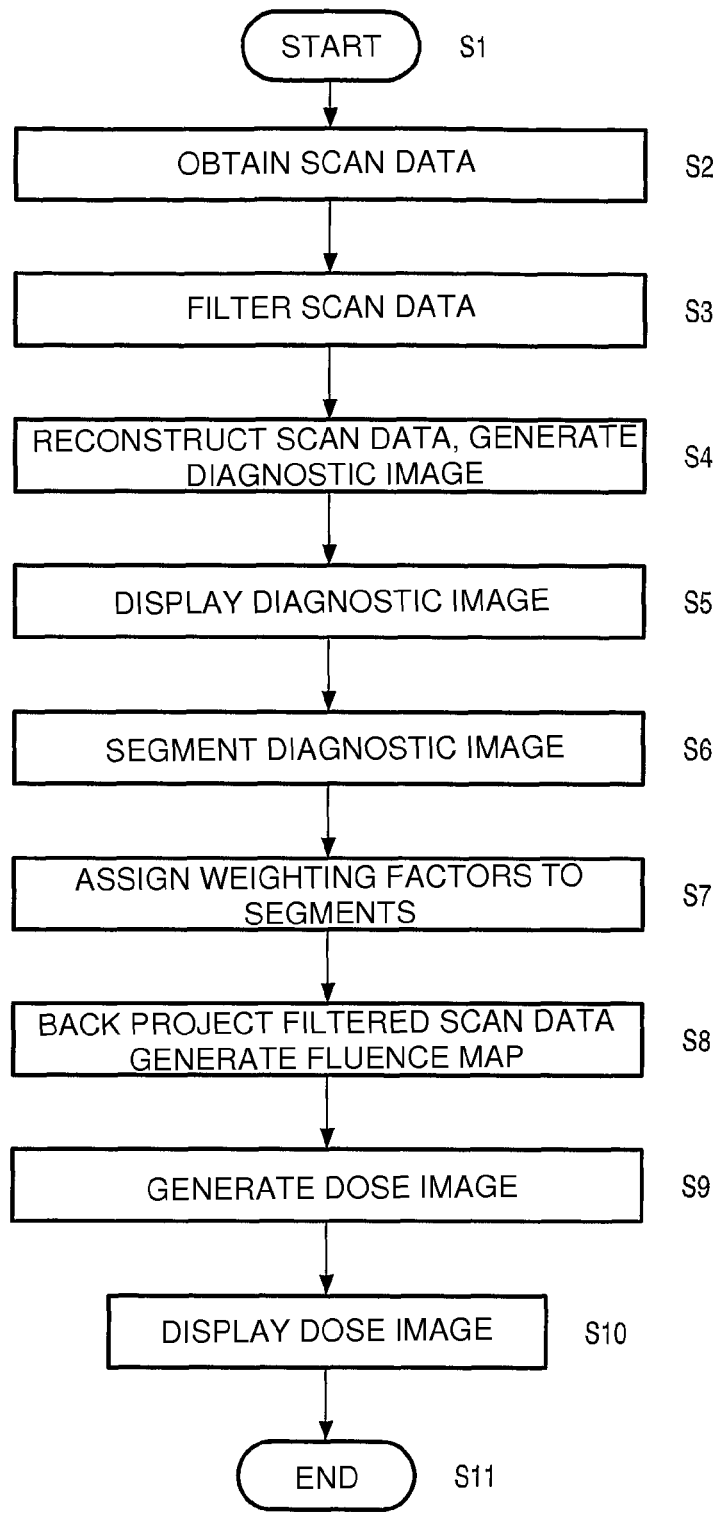
FIG. 3 is a flow chart illustrating an exemplary embodiment of a sequence of steps executed by the CT imaging system of FIGS. 1 and 2, to determine a local patient dose applied to a patient.

Image information or data provided by the data acquisition system 22 and/or the image reconstructor 24, is referred to as "scan data" in the following:

FIG. 3 shows a flow chart illustrating an exemplary embodiment of a sequence of steps of a method according to an exemplary embodiment of the present invention, executed by the CT system shown in FIGS. 1 and 2, to determine a local patient dose applied to the patient 12. The steps S1 to S11 are preferably executed in the data acquisition system 22, the dose reconstructor 40, the image reconstructor 24 and/or the computer 26. For storing and outputting, the output device 32 and the data storage 28 may be used. After the start in step S1, the method continues to step S2, where the scan data is obtained in known manner. Then, the method continues to step S3, where the scan data is filtered in known manner. Then, in a subsequent step S4, a tomographic reconstruction on the basis of the filtered scan data is carried out, in order to determine the diagnostic image of the area of interest of the patient. Usually, the tomographic reconstruction is such that a diagnostic image is generated with grey levels indicating Hounsfield units. After generation of the diagnostic image, the method continues to step S5, where the diagnostic image is output to a user or clinician for, e.g. diagnostic purposes.

Then, the method continues to steps S6 to S9 where the data is prepared for dose reconstruction.

In step S6, the diagnostic image is segmented into anatomical structures assigned to its voxels. In other words, the diagnostic image is segmented to "material", where a raw classification (e.g. metal, bone, water, air) based on Hounsfield-thresholds may be sufficient for this purpose.

In order to transform a fluence F to dose D, dose weighting factors (as indicated as factor prior to the fluence exponential function in the following formulae) are assigned to the anatomical structures in step S7, based on the already obtained raw segmentation according to material. This may be done by referring to predetermined tables linking the respective anatomical structures to predetermined dose-weighting factors. Anatomical structures are, e.g. bones, muscles, spaces or accumulations of blood.

Thus, for example a different dose-weighting factor may be assigned to muscles which are less prone to be damaged by the x-ray beam than, for examples organs like the liver or parts of the brain. In general, the dose-weighting factors should be determined such that they account both for differences between locally absorbed energy and photon attenuation of the respective anatomical structure and for biologically different sensitivity to dose absorption.

In step S8, the filtered scan data determined in step S3 is back-projected in a way appropriatley for dose reconstruction and a fluence map is reconstructed on the basis of this back-projection. Since the scan data is filtered in the same way as in step S3 (for simplicity, but not necessarily with the same filter kernel) as for reconstructing the Hounsfield image, the filtered data from image reconstruction may be saved in step S3 and re-used here. Advantageously, this allows to reduce the amount of arithmetic calculations.

A straight-forward calculation of total absorbed dose D at a position x in the patient volume carried out in step S8 (S6-S9)—directly expressed by means of the original scan data—can be described with the following equations:

$$D(\underline{x}) = S_0 \mu^a * \int d\theta e^{-\int_0^\infty d\lambda \mu(\underline{x} + \lambda \underline{e}_\theta)} \quad (1)$$

-continued $$= S_0 \mu^a * \int d\theta e^{-\int_0^\infty d\lambda \int dt [\sigma(t, \cdot) * k(\cdot)] ((\underline{x} + \lambda \underline{e}_\theta) \underline{e}_t^\perp \frac{1}{t})} \quad (2)$$

$\mu^\alpha$: material dependent absorption or scatter kernel (3)
$\theta$: gantry angle, i.e x-ray source position (4)
$\underline{e}_\theta$: unit vector in direction $\theta$ (5)
$\underline{e}_t^\perp$: unit vector orthogonal to direction t (6)
$\sigma(\ )$: scan data (7)
$k(\ )$: filter kernel (8)

$$d(x, \theta) = \int dt \int_0^\infty \underbrace{d\lambda [\sigma(t, \cdot) * k(\cdot)] \left( x \underline{e}\frac{1}{t} + \lambda \sin(\theta - t) \right)}_{=g(t, \tilde{\lambda}, x \underline{e}\frac{1}{t})} \quad (9)$$

$$= \int_0^\infty d\tilde{\lambda} \int dt \frac{1}{|\sin(\theta - t)|} g\left(t, \tilde{\lambda}, x \underline{e}\frac{1}{t}\right) \quad (10)$$

$$= \int d\tilde{\lambda} h(\theta, \tilde{\lambda}, x) \quad (11)$$

$g(\ )$: convolution as known from image reconstruction (12)
$h(\ )$: point-wise convolution with inverse sinus (13)

In this realisation example, instead of ray-tracing as will be described with reference to FIG. 4, the filtered scan data is re-used for dose reconstruction. The fluence F in x is integrated over all views similar to the back-projection method of image reconstruction.

Then, the method continues to step S9, in which a dose image is determined in accordance with the above formulae. The dose image determined in step S9 shows local patient doses applied to the patient. The dose image is determined by using the dose-weighting factors and the fluence map.

After the determination of the fluence map, the method continues to step S10, where the dose-image is output. Then, the method continues to step S11, where it ends.

According to another exemplary embodiment of the method of determining a local patient dose applied to a patient according to the present invention, the reconstruction of the fluence map and the segmentation of the diagnostic image into anatomical structures may be carried out in parallel. This allows for a very fast computation of the dose image.

Figure 4:
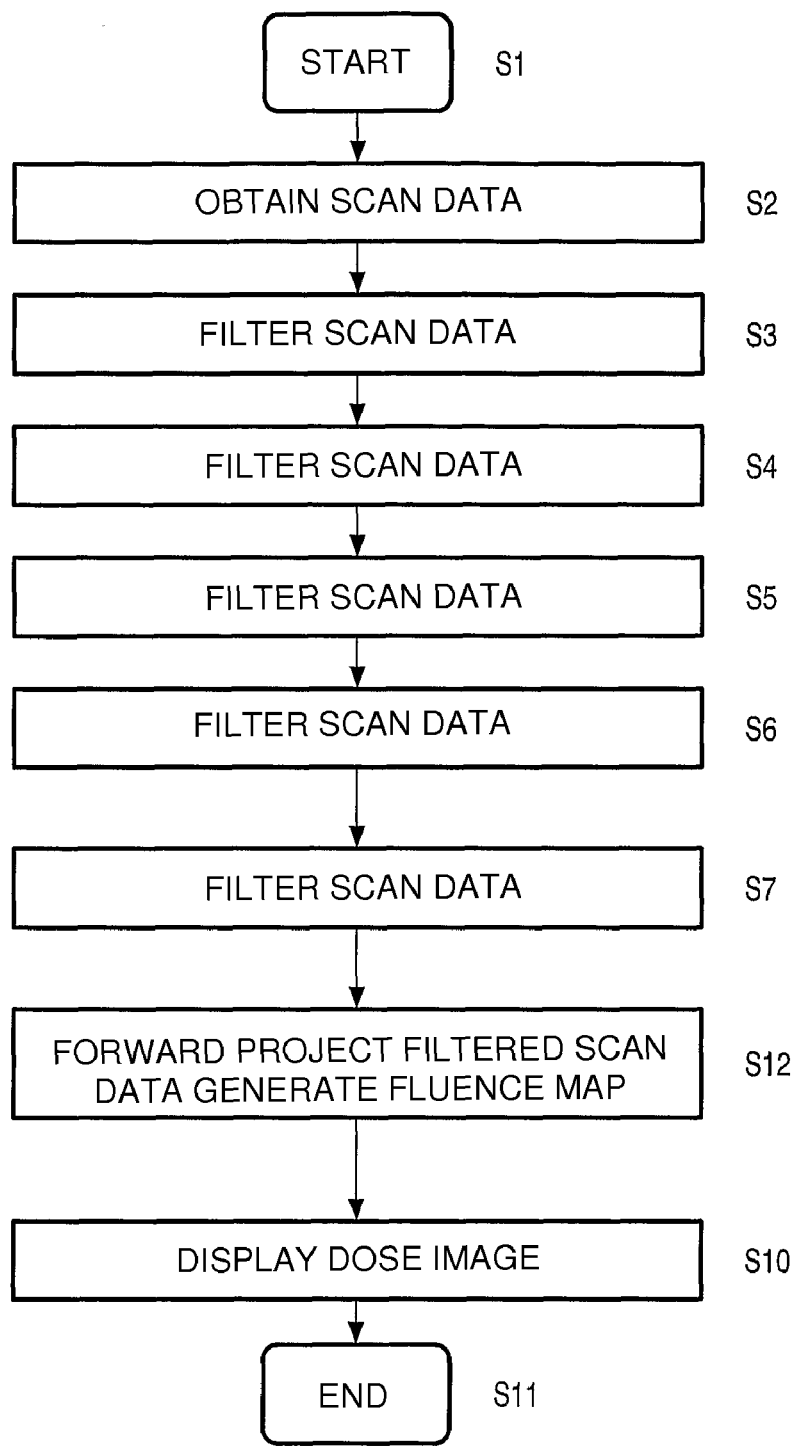
FIG. 4 is a flow chart illustrating another exemplary embodiment of a sequence of steps executed by the CT imaging system of FIGS. 1 and 2, to determine a local patient dose applied to a patient.

FIG. 4 shows a flow chart illustrating another exemplary embodiment of a sequence of steps of a method according to an exemplary embodiment of the present invention, executed by the CT system shown in FIGS. 1 and 2, to determine a local patient dose applied to the patient 12. Step 12 is preferably executed in the data acquisition system 22, the dose reconstructor 40, the image reconstructor 24 and/or the computer 26. For storing and outputting, the output device 32 and the data storage 28 may be used. Steps S1 to S7 and S10 to S11 are the same as described with reference to FIG. 4.

Firstly, in steps S6 and S7, the reconstructed image is segmented according to "material", where a raw classification (e.g. metal, bone, water, air) based on Hounsfield-thresholds is sufficient for this purpose, but more elaborated methods may be used, and dose-weighting factors are assigned to the anatomical structures. Then, in step S12, for each position of the gantry where a view has been generated, the x-ray source spectrum as known from calibration data is ray-traced through the simulated patient volume as known from step S4, separated into voxels with assigned material and corresponding attenuation coefficients. The absorbed dose is integrated for each voxel. Then, a dose image is determined which is output in the subsequent step S10. In other words, in step S12 the x-ray spectrum is forward-projected and the fluence map is reconstructed on basis of the segmented diagnostic image and then the dose image is determined that shows local patient doses applied to the patient using the dose-weighting factors and the fluence map.

In brief, according to the present invention, the method/apparatus make two-fold use out of the measured scan data. Namely, the scan data is reconstructed into a diagnostic image. Also, the scan data is back-projected into the patient volume, using the attenuation information of the diagnostic image forming a spatially varying photon fluence map, as being produced by the x-ray beam incident on the patient. In parallel, the diagnostic image may be segmented into anatomical factors, to which dose-weight factors are assigned which account for the difference between locally absorbed energy and photon attenuation. The locally absorbed dose is then calculated on the basis of the fluence map and the corresponding dose weights.

Preferably, the above method/apparatus may be used for CT systems.

The invention claimed is:

1. A method of determining a local patient dose applied to a patient in a diagnostic computed tomography scan of an area of interest of the patient, the method comprising the steps of:
   segmenting an image of an area of interest of the patient, wherein the image of the area of interest is determined from scan data obtained in the diagnostic computed tomography scan;
   determining a fluence map on the basis of the image of the area of interest; and
   using the segmented image and the fluence map to determine a dose image showing local patient doses applied to the patient in the scan.

2. The method according to claim 1, wherein the steps of segmenting the image of the area of interest of the patient further comprises the steps of:
   segmenting the image of the area of interest into anatomical structures in the area of interest of the patient; and
   assigning dose-weighting factors to the anatomical structures segmented in the image of the area of interest.

3. The method according to claim 2, wherein the anatomical structures include one or more of bone, muscles, and accumulation of blood.

4. The method according to claim 1, wherein the step of determining the dose image showing local patient doses applied to the patient further comprises the steps of:
   determining the dose image showing local patient doses applied to the patient on the basis of the fluence map and the dose-weighting factors.

5. The method according to claim 1, wherein the image of the area of interest of the patient has grey levels indicating Hounsfield units and the fluence map is determined by filtering the scan data and back-projecting it using information obtained from the previously determined image.

6. The method according to claim 1, further comprising the steps of determining a fluence map on the basis of the image of the area of interest of the patient temporally in parallel with segmenting the image of the area of the interest of the patient.

7. An image processing device, comprising:
   a memory for storing scan data;
   an image processor for determining a local patient dose applied to a patient in a computed tomography scan, which processor performs the following operations:
   segmenting a diagnostic image of an area of interest of the patient, wherein the diagnostic image of the area of interest is determined using scan data obtained in the computed tomography scan and wherein the diagnostic image is segmented into anatomical structures in the area of interest in the patient;
   assigning dose-weighting factors to the anatomical structures segmented in the diagnostic image;
   integrating an absorbed dose for each of a voxel the anatomical structures; and
   determining a dose image showing local patient doses applied to the patient in the scan using: the segmented diagnostic image, the assigned dose-weighting factors and the integrated absorbed dose.

8. The image processing device according to claim 7, further performing the operation of:
   determining a fluence map on the basis of the diagnostic image of an area of interest of the patient; and
   determining the dose image showing local patient doses applied to the patient on the basis of the fluence map and the dose-weighting factors.

9. The image processing device according to claim 7, wherein the image processing device is part of a computed tomography system.

10. The image processing device according to claim 7, further performing the operation of:
    determining a fluence map on the basis of the diagnostic image of the area of interest of the patient temporally in parallel with segmenting the diagnostic image of the area of interest of the patient.

11. The image processing device according to claim 7, further performing the operation of:
    determining a fluence map based on at least in part on dose-weighting factors assigned to portions of the segmented diagnostic image.

12. The image processing device according to claim 11, wherein different dose-weighting factors are assigned to different anatomical structures in the segmented diagnostic image.

13. The image processing device according to claim 7, wherein for each of at least one position of a gantry where the diagnostic image is generated an x-ray source spectrum is ray-traced through the area of interest of the patient for separation into voxels.

14. The image processing device according to claim 13, wherein each voxel is assigned corresponding attenuation coefficients.

15. The image processing device according to claim 7, wherein an x-ray spectrum is forward-projected on the basis of the segmented diagnostic image to determine the dose image.

16. A computer readable medium encoded with a computer program for an image processing device, wherein the computer program determines a local patient does applied to a patient in a computed tomography scan, the computer program comprising the steps of:
    segmenting a diagnostic image of an area of interest of the patient, wherein the diagnostic image is determined using scan data obtained in the computed tomography scan;
    determining a fluence map on the basis of the diagnostic image; and
    determining a dose image showing local patient doses applied to the patient in the scan by using the segmented diagnostic image and the fluence map.

17. The computer readable medium of claim 16, wherein the computer program further comprises the step of segmenting the diagnostic image in the area of interest of the patient into anatomical structures.

18. The computer readable medium of claim 17, wherein the computer program further comprises the step of assigning different dose-weighting factors to different anatomical structures in the area of interest of the patient.

19. The computer readable medium of claim 18, wherein the computer program further comprises the step of generating a fluence map as a function of the assigned dose-weighting factors.

20. The computer readable medium of claim 16, wherein the determined dose image shows local patient doses applied to the patient during a diagnostic scan.

* * * * *